(12) United States Patent
Choi

(10) Patent No.: US 8,821,160 B2
(45) Date of Patent: Sep. 2, 2014

(54) NANO BUBBLE GENERATING NOZZLE AND ORAL CLEANING DEVICE INCLUDING THE SAME

(76) Inventor: Jeng Soo Choi, Hwaseong-si (KR)

( * ) Notice: Subject to any disclaimer, the term of this patent is extended or adjusted under 35 U.S.C. 154(b) by 0 days.

(21) Appl. No.: 13/641,854

(22) PCT Filed: Jan. 24, 2011

(86) PCT No.: PCT/KR2011/000458
§ 371 (c)(1),
(2), (4) Date: Oct. 17, 2012

(87) PCT Pub. No.: WO2011/132846
PCT Pub. Date: Oct. 27, 2011

(65) Prior Publication Data
US 2013/0034829 A1  Feb. 7, 2013

(30) Foreign Application Priority Data
Apr. 23, 2010  (KR) .................. 10-2010-0037819

(51) Int. Cl.
*A61C 17/00* (2006.01)
*B05B 7/04* (2006.01)
*B05B 1/30* (2006.01)
*A61C 17/02* (2006.01)
*B05B 15/00* (2006.01)

(52) U.S. Cl.
CPC ........... *A61C 17/0202* (2013.01); *B05B 7/0425* (2013.01); *B05B 1/3013* (2013.01); *B05B 15/008* (2013.01); *A61C 17/0217* (2013.01)
USPC ......................................................... 433/80

(58) Field of Classification Search
USPC ......... 433/80–90, 215, 216; 261/76, DIG. 75, 261/77; 446/15, 21; 366/163.2; 137/888; 601/162–165
See application file for complete search history.

(56) References Cited

U.S. PATENT DOCUMENTS

| | | | | |
|---|---|---|---|---|
| 2,854,992 A | * | 10/1958 | Hewitt | 137/395 |
| 3,547,409 A | * | 12/1970 | Jacuzzi | 366/160.1 |
| 3,716,190 A | * | 2/1973 | Lindlof | 239/2.2 |
| 4,867,918 A | * | 9/1989 | Kiyonaga et al. | 261/76 |
| 4,903,688 A | * | 2/1990 | Bibby et al. | 601/162 |
| 5,203,698 A | * | 4/1993 | Blake et al. | 433/88 |
| 2004/0022669 A1 | * | 2/2004 | Ruan et al. | 422/22 |
| 2008/0014627 A1 | * | 1/2008 | Merchant et al. | 435/259 |
| 2010/0273125 A1 | * | 10/2010 | Janssen et al. | 433/80 |

FOREIGN PATENT DOCUMENTS

| | | |
|---|---|---|
| JP | 2008-161831 A | 7/2008 |
| JP | 2009-082903 A | 4/2009 |
| KR | 10-0798994 B1 | 1/2008 |
| KR | 10-2010-0007211 A | 1/2010 |

* cited by examiner

*Primary Examiner* — Yogesh Patel
(74) *Attorney, Agent, or Firm* — Novick, Kim & Lee, PLLC; Jae Youn Kim

(57) ABSTRACT

Disclosed is a nano bubble generating nozzle including: a passage passing through an interior thereof to provide a flow path through which liquid flows; a nano bubble generating part corresponding to a part of the passage, and formed such that a cross-section of the nano bubble generating part becomes small and then large again along a flow path of liquid so that the nano bubble generating part has a pressure lower than an external pressure of the nozzle body; and a gas inlet formed in the nozzle body, and connected to the nano bubble generating part so that gas is introduced into the nano bubble generating part due to a difference between an external pressure of the nozzle body and a pressure in the nano bubble generating part.

5 Claims, 7 Drawing Sheets

NANO BUBBLE GENERATING NOZZLE AND ORAL CLEANING DEVICE INCLUDING THE SAME

BACKGROUND OF THE INVENTION

1. Field of the Invention

The present invention relates to a nano bubble generating nozzle and an oral cleaning device including the same, and more particularly to a nano bubble generating nozzle which mixes gas with flowing liquid so that the liquid can contain nano bubble and an oral cleaning device including the same.

2. Description of the Prior Art

Generally, a bubble generating device refers to a device for generating and providing bubbles having various sizes.

The bubble generating device is used for various purposes according to a need of a user. For example, the bubble generating device may be used to provide bubbles into a washing tub to improve washing force, may be used for a cleaning operation for providing bubbles into a bath tub to improve a bathing effect, or may be used for a purpose of purifying water.

The bubble generating device mixes liquid obtained by pressing gas so that the gas is solved therein with circulating liquid and then reduces the pressure of the liquid so that the liquid is ejected while bubbles are contained in the flowing liquid.

However, the liquid in which the gas is pressed and solved needs to be mixed with the liquid circulating again, and after liquid in which the gas is pressed and solved is mixed with the circulating liquid, the pressure of the gas needs to be reduced again so that the mixed liquid is ejected.

That is, a high-pressure pump for pressing gas needs to be used to press and solve the gas in liquid. However, since gas needs to be contained in liquid by using a high-performance high-pressure pump to decrease sizes of bubbles, a configuration of the device becomes complex and manufacturing costs increase.

Further, in a device which uses a shear force of a rotary blade to generate bubbles after liquid obtained by pressing and solving gas and circulating liquid are mixed, the rotary blade as well as the high-pressure pump is necessary to generate cavitations. Accordingly, since a separate drive unit for driving the rotary blade is necessary, the configuration of the device becomes more complex.

In addition, maintenance costs of the rotary blade increase due to rapid corrosion and severe vibrations of a blade accompanied when the cavitations are generated.

SUMMARY OF THE INVENTION

Accordingly, the present invention has been made to solve the above-mentioned problems occurring in the prior art, and an object of the present invention is to provide a nano bubble generating nozzle which can introduce gas into flowing liquid without using a separate unit for mixing bubbles to generate nano bubbles.

Accordingly, the present invention provide a nano bubble generating nozzle by which noise and manufacturing costs generated when nano bubbles are mixed can be reduced, while realizing miniaturization.

The present invention also provide a nano bubble generating nozzle by which a phenomenon where nano bubbles generated by growth and breaking of nano bubble nuclei disappear before a discharging operation can be mitigated.

Meanwhile, the present invention provides an oral cleaning device which can discharge cleaning liquid containing nano bubbles.

In addition, the present invention also provides an oral cleaning device which can be simplified and miniaturized.

In order to accomplish this object, there is provided a nano bubble generating nozzle including: a passage passing through an interior thereof to provide a flow path through which liquid flows; a nano bubble generating part corresponding to a part of the passage, and formed such that a cross-section of the nano bubble generating part becomes small and then large along a flow path of liquid so that the nano bubble generating part has a pressure lower than an external pressure of the nozzle body; and a gas inlet formed in the nozzle body, and connected to the nano bubble generating part so that gas is introduced into the nano bubble generating part due to a difference between an external pressure of the nozzle body and a pressure in the nano bubble generating part.

The gas inlet corresponds to a communication hole formed in a radial direction of the nozzle body and connected to the nano bubble generating part, and the communication hole is formed such that a cross-section thereof is smaller than or equal to a minimum cross-section of the nano bubble generating part to prevent introduction of the liquid flowing through the nano bubble generating part.

A ratio of a diameter of a portion of the nano bubble generating part corresponding to a minimum cross-section and a diameter of the passage formed in the nozzle body may be 1:2 to 1:4.

The nano bubble generating nozzle further includes: a dispersing member mounted to the gas inlet to disperse the gas introduced into the gas inlet so that the gas introduced when the gas in the nano bubble generating part is mixed can be mixed with the liquid.

The dispersing member is formed of a porous material having a diameter smaller than 1 μm so that the penetrating gas can be made fine.

The gas inlet includes: an installation recess formed on a side surface of the nozzle body such that the dispersing member is installed therein; a cover member coupled to the installation recess, and including a gas inlet hole through which gas is introduced; and a communication hole extending from the installation recess to communicate the nano bubble generating part with the installation recess.

In accordance another aspect of the present invention, there is provided an oral cleaning device including: a cleaning device body including a cleaning liquid inlet through which cleaning liquid is introduced, a cleaning liquid ejection hole from which liquid containing nano bubbles is discharged, and a cleaning liquid passage connecting the cleaning liquid inlet and the cleaning liquid ejection hole; and a nano bubble generating nozzle connected to the cleaning liquid passage such that nano bubbles are contained in the flowing cleaning liquid by introducing gas due to a difference from an external pressure.

The nano bubble generating nozzle includes: a nozzle body including a passage passing through an interior thereof to provide a flow path through which liquid flows; a nano bubble generating part corresponding to a part of the passage, and formed such that a cross-section of the nano bubble generating part becomes small and then large along a flow path of liquid so that the nano bubble generating part has a pressure lower than an external pressure of the nozzle body; and a gas inlet connected to the nano bubble generating part so that gas is introduced into the nano bubble generating part due to a difference between an external pressure of the nozzle body and a pressure in the nano bubble generating part.

The nano bubble generating nozzle further includes: a dispersing member mounted to the gas inlet to disperse the gas introduced into the gas inlet so that the gas introduced can be mixed with the liquid.

The dispersing member is formed of a porous material having a diameter smaller than 1 μm so that the penetrating gas can be made fine.

The gas inlet includes: an installation recess formed on a side surface of the cleaning device body; a gas inlet member coupled to the installation recess, and including a gas flow passage through which gas is introduced, and a mounting recess where the dispersing member is installed; and a communication hole extending from the installation recess to communicate the nano bubble generating part with the installation recess.

The communication hole is formed such that a cross-section thereof is smaller than or equal to a minimum cross-section of the nano bubble generating part to prevent introduction of the liquid flowing through the nano bubble generating part.

A ratio of a diameter of a portion of the nano bubble generating part corresponding to a minimum cross-section and a diameter of the passage formed in the nozzle body may be 1:2 to 1:4.

The gas inlet further includes an air filter installed at an end of the gas flow passage to purify introduced air.

The oral cleaning device further includes: an opening/closing unit mounted to the mounting part provided in the cleaning device body to be connected to the cleaning liquid passage so as to open and close the cleaning liquid passage.

The opening/closing unit includes: an opening/closing member slidably coupled to the cleaning device body along a guide part provided in the cleaning device body to open and close the cleaning liquid passage; a support member fixedly coupled to the cleaning device body to be disposed at an upper portion of the opening/closing member; a resilient member mounted between the opening/closing member and the support member to provide a resilient force to the opening/closing member; and a sealing member mounted to a lower end of the opening/closing member to prevent the cleaning liquid from being discharged through the guide part.

According to the nano bubble generating nozzle of the present invention, since gas may be introduced into liquid flowing along the nano bubble generating part through the gas inlet due to a pressure difference between the nano bubble generating part and the outside of the nozzle body, the gas can be introduced into the flowing liquid without using a separate unit for mixing bubbles to generate nano bubbles.

That is, the gas can be introduced into the flowing liquid without using a separate device, such as a compression pump for compressing the gas, for mixing bubbles, vibrations generated by a separate unit can be reduced.

In addition, the gas introduced into the gas inlet is made fine through the dispersing member to be introduced into the liquid, thereby improving a generation rate of the nano bubbles.

Further, since the gas can be introduced into the flowing liquid without using a separate unit for mixing bubbles to generate nano bubbles, noise generated by a separate unit for introducing the gas can be reduced, and manufacturing costs can be reduced and the nano bubble generating nozzle can be miniaturized.

In addition, since the gas can be introduced into the flowing liquid without using a separate device, such as a compression pump for compressing the gas, for mixing bubbles, vibrations generated by a separate unit can be reduced, and accordingly, a phenomenon where the generated nano bubbles disappear before a discharging operation can be mitigated.

Further, since a distance by which nano bubbles are moved can be reduced by simplifying the structure of the nano bubble generating nozzle, a phenomenon where nano bubbles generated by growth and breaking of nano bubble nuclei in the passage of the nozzle body disappear before a discharging operation can be mitigated.

That is, since a distance by which the generated nano bubbles are moved can be reduced by simplifying the structure, a phenomenon where the nano bubbles disappear can be mitigated.

Meanwhile, according to the oral cleaning device of the present invention, the cleaning liquid containing nano bubbles can be discharged through the nano bubble generating nozzle.

In addition, since the structure of the nano bubble generating nozzle for generating nano bubbles is simple, the cleaning liquid containing nano bubbles can be discharged and the device can be miniaturized at the same time.

Further, as the liquid containing nano bubbles can be discharged, an effect by which the liquid containing nano bubbles reaches a target object, such as teeth or gums, so that the nano bubbles disappear, that is, the vibration and negative ion effect can be realized.

BRIEF DESCRIPTION OF THE DRAWINGS

The above and other objects, features and advantages of the present invention will be more apparent from the following detailed description taken in conjunction with the accompanying drawings, in which.

DETAILED DESCRIPTION OF THE PREFERRED EMBODIMENTS

Hereinafter, exemplary embodiments of the present invention will be described in detail with reference to the accompanying drawings. Meanwhile, the spirit of the present invention is not limited to the suggested embodiments, but those skilled in the art to which the present invention pertains can suggest another retrogressive invention or another embodiment which falls within the spirit of the present invention through addition, modification, and deletion of another component without departing from the spirit of the present invention.

A detailed description of known functions and configurations of the present invention will be omitted when it may make the subject of the present invention unclear.

Hereinafter, a nano bubble generating nozzle according to an embodiment of the present invention will be described with reference to the drawings.

Figure 1:
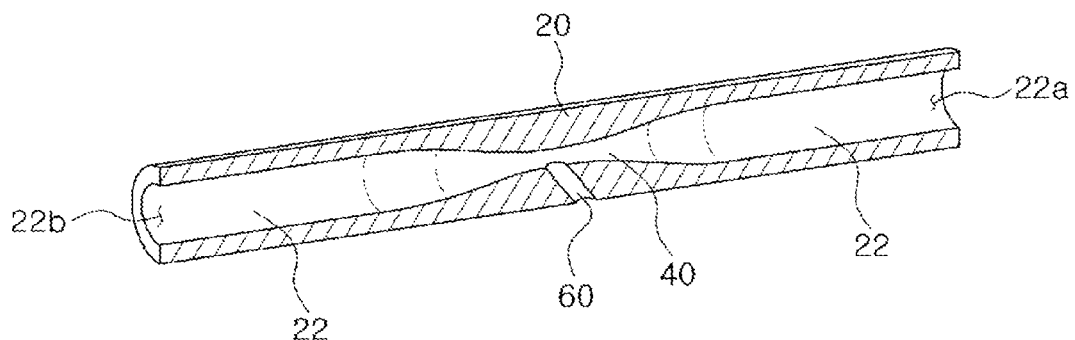
FIG. 1 is a cutaway perspective view illustrating a nano bubble generating nozzle according to an embodiment of the present invention.
Figure 2:
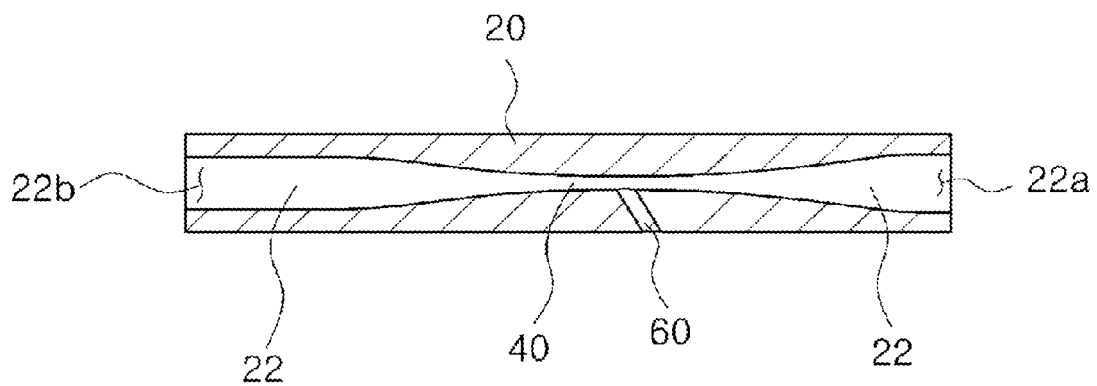
FIG. 2 is a sectional view illustrating the nano bubble generating nozzle according to the embodiment of the present invention.

FIG. 1 is a cutaway perspective view illustrating a nano bubble generating nozzle according to an embodiment of the present invention. FIG. 2 is a sectional view illustrating the nano bubble generating nozzle according to the embodiment of the present invention;

Referring to FIGS. 1 and 2, the nano bubble generating nozzle 10 according to the embodiment of the present invention includes a nozzle body 20, a nano bubble generating part 40, and a gas inlet 60.

The nozzle body 20 includes a passage 22 passing through an interior thereof to provide a flow path through which liquid flows. That is, the nozzle body 20 includes the passage 22 having a liquid inlet 22a through which liquid is introduced and a liquid outlet 22b from which liquid containing nano bubbles is discharged.

The nano bubble generating part 40 is a part of the passage 22, and is formed such that a cross-section of the nano bubble generating part 40 becomes small and then large again along a flow path of liquid so that the nano bubble generating part 40 has a pressure lower than an external pressure of the nozzle body 20.

That is, the nano bubble generating part 40 is formed such that a pressure in the nano bubble generating part 40 is lower than an external pressure due to a change in a diameter thereof. As an example, the nano bubble generating part 40 may have a venturi tube. Accordingly, a pressure in the nano bubble generating part 40 may be lower than an external pressure of the nozzle body 20.

As an example, when an external pressure of the nozzle body 20 is 1 atm (i.e. 1.033227 $kgf/cm^2$), a pressure in the nano bubble generating part 40 may be 0.3 to 0.5 $kgf/cm^2$. That is, when liquid flows through the nano bubble generating part 40 at a predetermined ejection speed or higher, a pressure in the nano bubble generating part 40 becomes lower than an external pressure of the nozzle body 20, in which case a pressure in the nano bubble generating part 40 may be preferably 0.3 to 0.5 $kgf/cm^2$.

That is, a pressure in the nano bubble generating part may be changed according to a pressure of fluid introduced through the passage of the nozzle body 20, that is, a pressure by which the fluid can be ejected at a predetermined ejection speed or higher, and may be a pressure lower than an external pressure of the nozzle body 20, that is, 1 atm.

Meanwhile, in order to generate nano bubbles, a ratio of a diameter of a portion of the nano bubble generating part 40 corresponding to a minimum cross-section and a diameter of the passage 22 formed in the nozzle body 20 may be 1:2 to 1:4.

As an example, when a diameter of the passage 22 formed in the nozzle body 20 is 2 mm, a diameter of the nano bubble generating part 40 corresponding to a minimum cross-section needs to be 1 mm or less. If a diameter of the nano bubble generating part 40 corresponding to a minimum cross-section is 1 mm or more, a nano bubble generating rate in the nano bubble generating part 40 is significantly reduced.

As another example, when a diameter of the passage 22 formed in the nozzle body 20 is 2 mm, a diameter of the nano bubble generating part 40 may be preferably 0.5 mm. In this case, an optimum nano bubble generating rate may be realized.

More preferably, a portion of the nano bubble generating part 40 corresponding to a minimum cross-section may have a diameter by which a pressure in the nano bubble generating part 40 may become lower than 1 atm, for example, a diameter by which a pressure in the nano bubble generating part 40 may become 0.3 to 0.5 $kgf/cm^2$.

Meanwhile, a flow rate of the liquid flowing through a region where a cross-section of the nano bubble generating part 40 is reduced becomes higher than a flow rate in the liquid inlet 22a. Accordingly, the gas introduced into the nano bubble generating part 40 may become fine so that a large amount of nano bubbles can be generated.

That is, the gas introduced into the nano bubble generating part 40 may become finer due to the liquid flowing faster. Thus, a larger amount of nano bubbles can be generated at the same flow amount due to an increase in flow rate.

The gas inlet 60 is formed in the nozzle body 20, and is connected to the nano bubble generating part 40 so that gas is introduced into the nano bubble generating part 40 due to a difference between an external pressure of the nozzle body 20 and a pressure in the nano bubble generating part 40.

The gas inlet 60 may be a communication hole formed in a radial direction of the nozzle body 20 and connected to the nano bubble generating part 40. That is, gas is introduced into the nano bubble generating part 40 through the gas inlet 60 corresponding to a communication hole due to a difference between an external pressure of the nozzle body 20 and a pressure in the nano bubble generating part 40.

Meanwhile, in definition of directions, a lengthwise direction of the nozzle body 20 is a direction where the passage 22 is formed, that is, a direction of the liquid outlet 22b with respect to the liquid inlet 22a with reference to FIG. 2, a radial direction of the nozzle body 20 is an upward/downward direction of the nozzle body 20 with respect to the passage 22 with reference to FIG. 2, and a circumferential direction of the nozzle body 20 is a rotation direction along an outer peripheral surface of the nozzle body 20.

The gas inlet 60 is formed such that a cross-section thereof is smaller than or equal to a minimum cross-section of the nano bubble generating part 40 to prevent the liquid flowing through the nano bubble generating part 40 from being introduced into the gas inlet 60.

That is, as a cross-section of the nano bubble generating part 40 decreases, a flow rate of the liquid flowing through the nano bubble generating part 40 increases but an internal resistance due to the nano bubble generating part 40 also increases. Accordingly, the fluid flowing along the nano bubble generating part 40 tends to flow to a part where an internal resistance is low.

Thus, when a diameter of the gas inlet 60 is larger than a diameter of the nano bubble generating part 40 at a portion having a minimum cross-section, the fluid flowing along the nano bubble generating part 40 may flow toward the gas inlet 60.

In this way, in order to prevent liquid from flowing toward the gas inlet 60, a diameter of the gas inlet 60 is the same as or smaller than a diameter of the nano bubble generating part 40 at a portion having a minimum cross-section.

Meanwhile, it has been exemplified in the embodiment that one gas inlet 60 is formed in the nozzle body 20, but the embodiment is not limited thereto but a plurality of gas inlets 60 may be formed in the nozzle body 20 along a circumferential direction of the nozzle body 20.

Meanwhile, sizes of the bubbles contained in the liquid ejected through the liquid outlet 22b of the nozzle body 20 may correspond to nano sizes or several μm to 50 μm.

Meanwhile, in a mechanism for generating bubbles having nano sizes, bubbles in micrometers units contained in the liquid ejected to the liquid outlet 22b are generally contracted by a surface tension and a pressure in the liquid and then are contracted into bubbles having nano sizes, and are finally broken.

Meanwhile, large micro bubbles (e.g. micrometer bubbles having a diameter of 50 μm) are broken without being contracted as the micro bubbles are moved fast to a surface of the shape of the liquid (e.g. the shape of the liquid discharged to have a funnel shape) ejected in the liquid, but the micro bubbles having a predetermined size or smaller are contracted into nano bubbles as the micro bubbles flows slowly to a surface in the liquid.

Thus, the bubbles contained in the liquid discharged to the liquid outlet 22b may be changed into nano bubbles before contacting a target object.

As a result, the liquid containing nano bubbles can reach the target object. Accordingly, the vibration and negative ion effect can be realized while the nano bubbles reach the target object and then disappear.

As described above, since bubbles may be generated through a small-sized nano bubble generating nozzle 10 having a passage 22a diameter of which is around 2 mm, nano bubbles having sizes in nano units can be generated.

In addition, since gas may be introduced into liquid flowing along the nano bubble generating part 40 through the gas inlet 60 due to a pressure difference between the nano bubble generating part 40 and the outside of the nozzle body 20, the gas can be introduced into the flowing liquid without using a separate unit for mixing bubbles to generate nano bubbles.

Further, since the gas can be introduced into the flowing liquid without using a separate unit for mixing bubbles to generate nano bubbles, noise generated by a separate unit for introducing the gas can be reduced and manufacturing costs can be reduced.

In addition, since the gas can be introduced into the flowing liquid without using a separate device, such as a compression pump for compressing the gas, for mixing bubbles, vibrations generated by a separate unit can be reduced, and accordingly, a phenomenon where the generated nano bubbles disappear can be mitigated.

In addition, the nano bubble generating nozzle 10 can be miniaturized.

Further, since a distance by which nano bubbles are moved can be reduced by miniaturizing the nano bubble generating nozzle 10, a phenomenon where nano bubbles generated by growth and breaking of nano bubble nuclei in the passage 22 of the nozzle body 20 disappear before a discharging operation can be mitigated.

That is, since a distance by which the generated nano bubbles are moved can be reduced by simplifying the structure, a phenomenon where the nano bubbles disappear can be mitigated.

Hereinafter, a nano bubble generating nozzle according to another embodiment of the present invention will be described with reference to the accompanying drawings. Meanwhile, a description of the same components as those of the above embodiment will be substituted and will not be described in detail.

Figure 3:
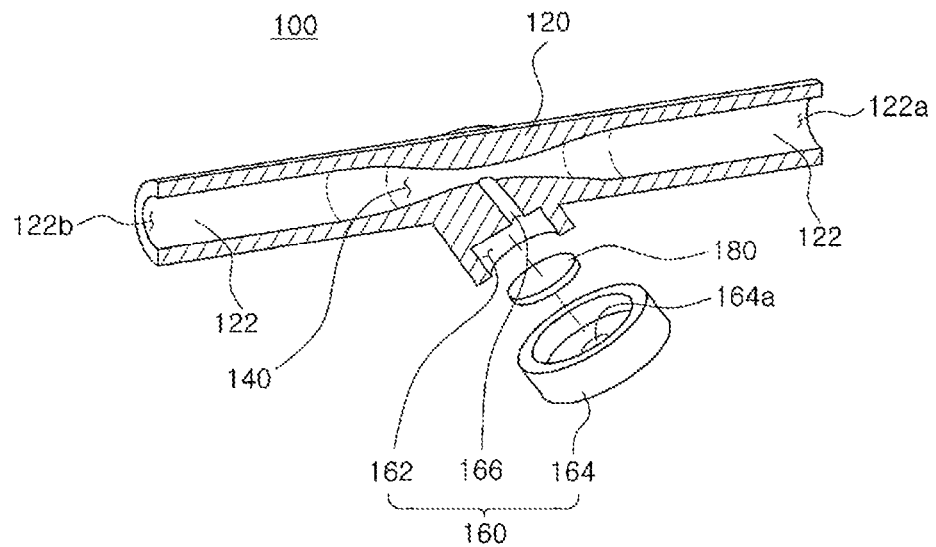
FIG. 3 is a cutaway perspective view illustrating a nano bubble generating nozzle according to another embodiment of the present invention.
Figure 4:
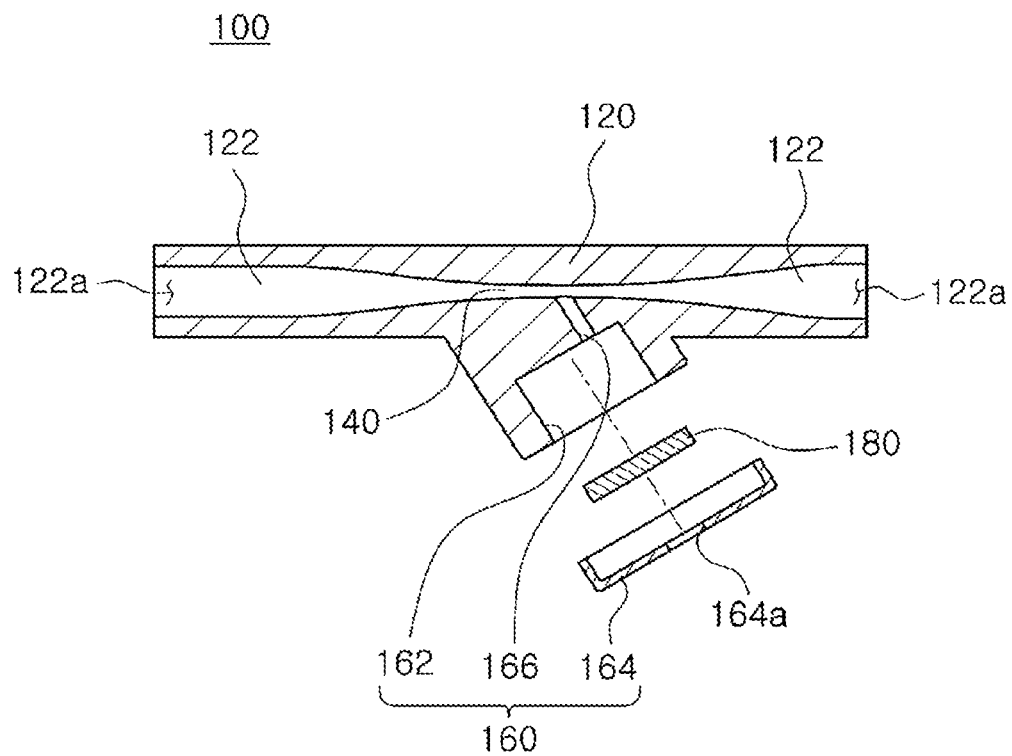
FIG. 4 is a sectional view illustrating the nano bubble generating nozzle according to the another embodiment of the present invention.

FIG. 3 is a cutaway perspective view illustrating a nano bubble generating nozzle according to another embodiment of the present invention. FIG. 4 is a sectional view illustrating the nano bubble generating nozzle according to the another embodiment of the present invention.

Referring to FIGS. 3 and 4, the nano bubble generating nozzle 100 according to the another embodiment of the present invention includes a nozzle body 120, a nano bubble generating part 140, a gas inlet 160, and a dispersing member 180.

Meanwhile, the nozzle body 120 and the nano bubble generating part 140 correspond to the same configurations of the nozzle body 20 and the nano bubble generating part 40 of the nano bubble generating nozzle 10 of the first embodiment of the present invention, and a detailed description thereof will be omitted here.

The gas inlet 160 is formed in the nozzle body 120, and is connected to the nano bubble generating part 140 so that gas is introduced into the nano bubble generating part 140 due to a difference between an external pressure of the nozzle body 120 and a pressure of the nano bubble generating part 140.

Meanwhile, as in the first embodiment, an external pressure of the nozzle body 120 may be 1 atm (i.e. (i.e. 1.033227 kgf/cm$^2$), a pressure in the nano bubble generating part 40 may be 0.3 to 0.5 kgf/cm$^2$.

Meanwhile, the gas inlet 160 may include an installation recess 162, a cover member 164, and a communication hole 166.

The installation recess 162 is formed on a side surface of the nozzle body 120 such that the dispersing member 180 can be installed therein. That is, the installation recess 162 is formed on a side surface of the nozzle body 120 to have a shape corresponding to the shape of the dispersing member 180.

The cover member 164 is coupled to the installation recess 162, and includes a gas inlet hole 164a through which gas is introduced. That is, the cover member 164 serves to prevent separation of the dispersing member 180 installed in the installation recess 162, and includes at least one gas inlet hole 164a so that gas can be introduced into the installation recess 162.

That is, although one gas inlet hole 164a is illustrated, the embodiment is not limited thereto but a plurality of gas inlet holes 164a may be provided.

The communication hole 166 extends from the installation recess 162 to communicate the nano bubble generating part 140 with the installation recess 162.

The communication hole 166 is formed such that a cross-section thereof is smaller than or equal to a minimum cross-section of the nano bubble generating part 140 to prevent introduction of the liquid flowing through the nano bubble generating part 140.

That is, as a cross-section of the nano bubble generating part 40 decreases, a flow rate of the liquid flowing through the nano bubble generating part 40 increases but an internal resistance due to the nano bubble generating part 40 also increases. Accordingly, the fluid flowing along the nano bubble generating part 40 tends to flow to a part where an internal resistance is low.

Thus, when a diameter of the communication hole 166 is larger than a diameter of the nano bubble generating part 40 at a portion having a minimum cross-section, the fluid flowing along the nano bubble generating part 40 may flow toward the communication hole 166.

In this way, in order to prevent liquid from flowing toward the communication hole 166, a diameter of the communication hole 166 is the same as or smaller than a diameter of the nano bubble generating part 40 at a portion having a minimum cross-section.

The dispersing member 180 is mounted to the gas inlet 160, and disperses the gas introduced into the gas inlet 160 so that the gas introduced when the gas in the nano bubble generating part 140 is mixed can be mixed with the liquid.

In more detail, the dispersing member 180 is installed in the installation recess 162 of the gas inlet 160, and disperses the gas introduced through the gas inlet hole 164*a* of the cover member 164 to make the gas fine primarily.

Thereafter, the gas having passed through the dispersing member 180 and having been made fine primarily is introduced into the nano bubble generating part 140 through the communication hole 166. Then, the gas introduced into the nano bubble generating part 140 is made fine secondarily by the liquid flowing along the nano bubble generating part 140 to be mixed with the flowing liquid.

That is, the gas having been made fine primarily and exiting from the communication hole 166 is made fine secondarily as if the gas is divided by the liquid of a relatively high speed flowing through the nano bubble generating part 140 to be mixed with the flowing liquid.

Meanwhile, the dispersing member 180 may be formed of a porous material having a diameter smaller than 1 μm so that the penetrating gas can be made fine.

As described above, as the gas introduced into the nano bubble generating part 140 through the dispersing member 180 can be made fine and be introduced into the nano bubble generating part 140, a generation rate of the nano bubbles can be improved.

Figure 5A:
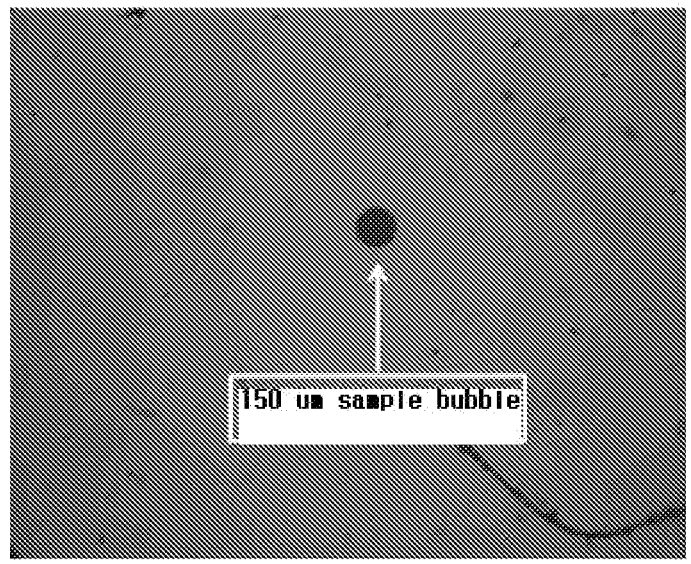
FIG. 5A illustrates an image of a 150 μm sample captured through a fluorescent microscope.
Figure 5B:
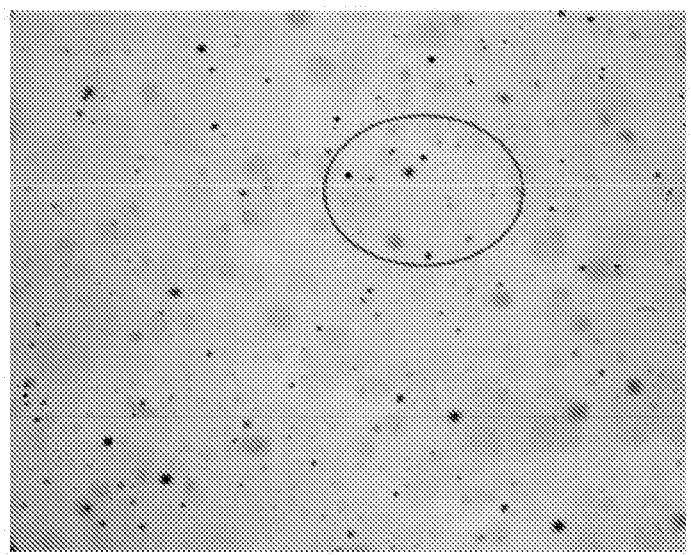
FIG. 5B illustrates an image of nano bubbles generated by the nano bubble generating nozzle according to the another embodiment of the present invention, which has been captured through a fluorescent microscope.

Meanwhile, an image acquired through a fluorescent microscope to identify sizes of nano bubbles generated through the nano bubble generating nozzle 100 according to the another embodiment of the present invention is disclosed in FIG. 5. FIG. 5A illustrates an image of a 150 μm sample captured through a fluorescent microscope, and FIG. 5B illustrates an image of nano bubbles generated by the nano bubble generating nozzle according to the another embodiment of the present invention, which has been captured through a fluorescent microscope.

In comparison of FIGS. 5A and 5B, the nano bubbles generated through the nano bubble generating nozzle take the form of black spots in FIGS. 5B, and it can be seen that sizes thereof is several μm to 50 μm as compared with a size of a 150 μm sample disclosed in FIG. 5A.

As described above, since gas is introduced into the nano bubble generating part 140 through the gas inlet 160 connected to the nano bubble generating part 140 due to a difference between an external pressure of the nozzle body 120 and a pressure of the nano bubble generating part 140, the gas can be introduced into the flowing liquid without using a separate unit for mixing of the bubbles to generate nano bubbles.

That is, gas can be introduced into liquid without using a separate unit, such as a compression pump for compressing the gas, for mixing the bubbles to generate nano bubbles.

In addition, the gas introduced into the gas inlet 160 is made fine primarily through the dispersing member 180 to be introduced into the liquid, thereby improving a generation rate of the nano bubbles.

Further, since the gas can be introduced into the flowing liquid without using a separate unit for mixing bubbles to generate nano bubbles, noise generated by a separate unit for introducing the gas can be reduced, and manufacturing costs can be reduced and the nano bubble generating nozzle can be miniaturized.

In addition, since the gas can be introduced into the flowing liquid without using a separate device, such as a compression pump for compressing the gas, for mixing bubbles, vibrations generated by a separate unit can be reduced, and accordingly, a phenomenon where the generated nano bubbles disappear before a discharging operation can be mitigated.

Further, since a distance by which nano bubbles are moved can be reduced by simplifying the structure of the nano bubble generating nozzle, a phenomenon where nano bubbles generated by growth and breaking of nano bubble nuclei in the passage 122 of the nozzle body 120 disappear before a discharging operation can be mitigated.

That is, since a distance by which the generated nano bubbles are moved can be reduced by simplifying the structure, a phenomenon where the nano bubbles disappear can be mitigated.

In addition, as the liquid containing nano bubbles can be discharged, an effect by which the liquid containing nano bubbles reaches a target object so that the nano bubbles disappear, that is, the vibration and negative ion effect can be realized.

Hereinafter, an oral cleaning device according to an embodiment of the present invention will be described with reference to the accompanying drawings.

Figure 6:
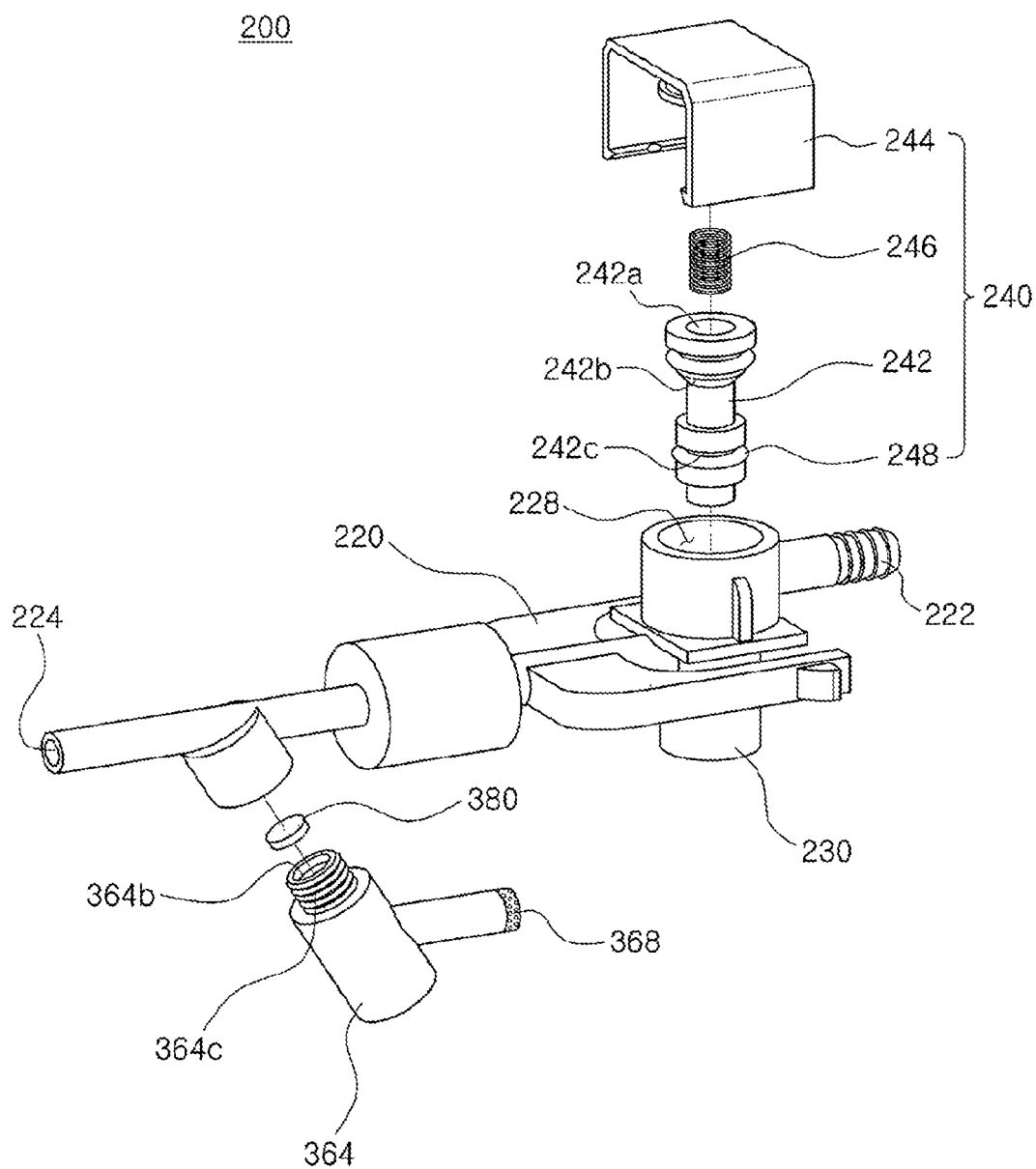
FIG. 6 is a perspective view illustrating an oral cleaning device according to an embodiment of the present invention.
Figure 7:
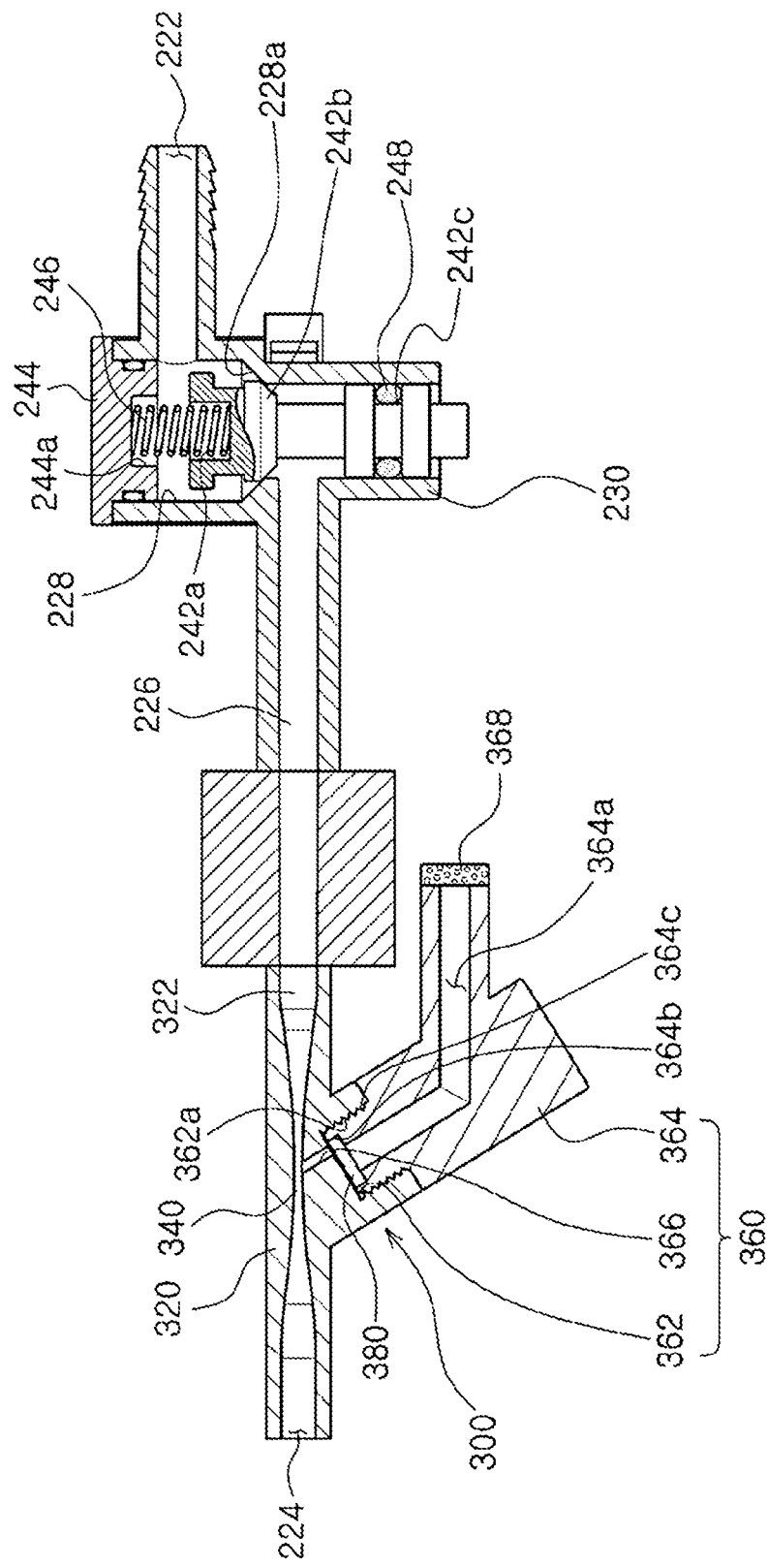
FIG. 7 is a sectional view illustrating the oral cleaning device according to the embodiment of the present invention.

FIG. 6 is a perspective view illustrating an oral cleaning device according to an embodiment of the present invention, and FIG. 7 is a sectional view illustrating the oral cleaning device according to the embodiment of the present invention.

Referring to FIGS. 6 and 7, the oral cleaning device 200 according to the embodiment of the present invention includes a cleaning device body 220, an opening/closing unit 240, and a nano bubble generating nozzle 300.

The cleaning device body 220 includes a cleaning liquid inlet 222 through which cleaning liquid is introduced, a cleaning liquid ejection hole 224 from which liquid containing nano bubbles is discharged, and a cleaning liquid passage 226 connecting the cleaning liquid inlet 222 and the cleaning liquid ejection hole 224.

That is, the cleaning liquid is introduced into the cleaning device body 220 through a cleaning liquid supply pipe (not illustrated) connected to the washing liquid inlet 222. Then, the cleaning liquid may be supplied by a supply pump (not illustrated).

Meanwhile, the cleaning device body 220 may include a mounting part 228 where the opening/closing unit 240 is installed.

The opening/closing unit 240 is mounted to the mounting part 228 provided in the cleaning device body 220 to be connected to the cleaning liquid passage 226 so as to open and close the cleaning liquid passage 226.

To this end, as an example, the opening/closing unit 240 may include an opening/closing member 242, a support member 244, a resilient member 246, and a sealing member 248.

The opening/closing member 242 is slidably coupled to the cleaning device body 220 along a guide part 230 provided in the cleaning device body 220 to open and close the cleaning liquid passage.

Meanwhile, the opening/closing member 242 may have a groove 242*a* by which one end of the resilient member 246 is supported on an upper surface thereof, and the opening/closing member 242 may be returned to an original position by the resilient member 246 one end of which is supported by the groove 242*a* to close the cleaning liquid passage 226.

The opening/closing member 242 may include an opening/closing part 242*b* having a shape corresponding to an inclined surface 228*a* provided in the mounting part 228 so that supply of the cleaning liquid can be started or interrupted by a slide movement thereof. That is, when the opening/closing part 242*b* contacts the inclined surface 228*a*, supply of the cleaning liquid is interrupted, whereas when the opening/closing part 242b is extracted from the inclined surface 228a, supply of the cleaning liquid is started.

Further, the opening/closing member 242 may include a concave part 242c disposed at a lower end of the opening/closing part 242b so that a sealing member 248 can be mounted thereto. Meanwhile, the concave part 242c can be moved in the guide part 230 to prevent cleaning liquid from being discharged to the outside of the cleaning device body 220.

The support member 244 is fixedly coupled to the cleaning device body 220 to be disposed at an upper portion of the opening/closing member 242. Further, the support member 244 may have a groove 244a formed at a location corresponding to the groove 242a of the opening/closing member 242 to support an opposite end of the resilient member 246.

Meanwhile, as described above, the resilient member 246 is mounted to support opposite ends of the grooves 242a and 244a provided in the opening member 242 and the support member 244 to return the opening/closing member 242 to an original position while providing a resilient force.

That is, if the opening/closing member 242 is pressed by a user, the resilient member 246 is compressed, in which case the opening/closing part 242b of the opening/closing member 242 is extracted from the guide member 228a so that the cleaning liquid can be supplied to a rear side.

Thereafter, if the pressing of the opening/closing member 242 is stopped by the user, the resilient member 246 is extended by the resilient force of the resilient member 246, and accordingly, the opening/closing part 242b of the opening/closing member 242 is introduced into the guide member 228a to interrupt supply of the washing liquid.

The sealing member 248 is mounted to a lower end of the opening/closing member 242 to prevent the cleaning liquid from being discharged through the guide part 230. As an example, the sealing member 248 may be an O-ring.

The nano bubble generating nozzle 300 is connected to the cleaning liquid passage 226, and nano bubbles are contained in the flowing cleaning liquid by introducing gas due to a difference from an external pressure.

To this end, as an example, the nano bubble generating nozzle 300 includes a nozzle body 320, a nano bubble generating part 340, a gas inlet 360, and a dispersing member 380.

The nano bubble generating part 340 is a part of the passage 322, and a cross-section thereof is reduced and expanded along a flow passage of the liquid to have a pressure lower than an external pressure of the cleaning device body 220.

Meanwhile, the nozzle body 320 and the nano bubble generating part 340 may be integrally formed with the cleaning liquid passage 226, and the nozzle body 320 having a passage 322 where the nano bubble generating part 340 is formed may be mounted to the cleaning device body 220.

Meanwhile, the nano bubble generating part 340 is formed such that a pressure in the nano bubble generating part 340 is lower than an external pressure of the cleaning device body 220 due to a change in a diameter thereof. As an example, the nano bubble generating part 340 may have a venturi tube. Accordingly, a pressure in the nano bubble generating part 340 may be lower than an external pressure of the nozzle body 320.

As an example, when an external pressure of the nozzle body 220 is 1 atm (i.e. 1.033227 kgf/cm$^2$), a pressure in the nano bubble generating part 240 may be 0.3 to 0.5 kgf/cm$^2$. That is, when liquid flows through the nano bubble generating part 240 at a predetermined ejection speed or higher, a pressure in the nano bubble generating part 240 becomes lower than an external pressure of the nozzle body 220, in which case a pressure in the nano bubble generating part 240 may be preferably 0.3 to 0.5 kgf/cm$^2$.

Meanwhile, in order to generate nano bubbles, a ratio of a diameter of a portion of the nano bubble generating part 340 corresponding to a minimum cross-section and a diameter of the passage 322 formed in the nozzle body 320 may be 1:2 to 1:4.

As an example, when a diameter of the passage 322 formed in the nozzle body 320 is 2 mm, a diameter of the nano bubble generating part 340 corresponding to a minimum cross-section needs to be 1 mm or less. If a diameter of the nano bubble generating part 340 corresponding to a minimum cross-section is 1 mm or more, a nano bubble generating rate in the nano bubble generating part 340 is significantly reduced.

As another example, a diameter of the passage 322 formed in the nozzle body 320 is 2 mm, a diameter of the nano bubble generating part 340 may be preferably 0.5 mm. In this case, an optimum nano buble generating rate may be realized.

Meanwhile, a flow rate of the liquid flowing through a region where a cross-section of the nano bubble generating part 340 is reduced becomes higher than a flow rate in the passage 322. Accordingly, the gas introduced into the nano bubble generating part 340 may become fine so that a large amount of nano bubbles can be generated.

That is, the gas introduced into the nano bubble generating part 340 may become finer due to the liquid flowing faster. Thus, a larger amount of nano bubbles can be generated at the same flow amount due to an increase in flow rate.

The gas inlet 360 is formed in the nozzle body 320, and is connected to the nano bubble generating part 340 so that gas is introduced into the nano bubble generating part 340 due to a difference between an external pressure of the nozzle body 320 and a pressure in the nano bubble generating part 340.

Meanwhile, the gas inlet 360 may include an installation recess 362, a gas inlet member 364, and a communication hole 366.

The installation recess 362 is formed on a side surface of the cleaning device body 220. A female screw portion 362a to be screw-coupled to the gas inlet member 364 may be formed on an inner surface of the installation recess 362.

The gas inlet member 364 may be coupled to the installation recess 362, and may include a gas flow passage 364a through which gas is introduced, and a mounting recess 364a where the dispersing member 380 is installed. A male screw portion 364c corresponding to the female screw portion 362a formed in the installation recess 362 may be formed at one end of the gas inlet member 364.

Meanwhile, the communication hole 366 extends from the installation recess 362, and communicates the nano bubble generating part 340 and the installation recess 362. The communication hole 366 is formed such that a cross-section thereof is smaller than or equal to a minimum cross-section of the nano bubble generating part 340 to prevent the liquid flowing through the nano bubble generating part 340 from being introduced.

That is, as a cross-section of the nano bubble generating part 340 decreases, a flow rate of the liquid flowing through the nano bubble generating part 340 increases but an internal resistance due to the nano bubble generating part 340 also increases. Accordingly, the fluid flowing along the nano bubble generating part 340 tends to flow to a part where an internal resistance is low.

Thus, when a diameter of the communication hole 366 is larger than a diameter of the nano bubble generating part 340 at a portion having a minimum cross-section, the fluid flowing along the nano bubble generating part 340 may flow toward the communication hole 366.

In this way, in order to prevent liquid from flowing toward the communication hole 366, a diameter of the communication hole 366 is the same as or smaller than a diameter of the nano bubble generating part 340 at a portion having a minimum cross-section.

Further, the gas inlet 360 may further include an air filter 368 installed at an end of the gas flow passage 363a to purify introduced air. That is, the gas inlet 360 may further include the air filter 368 for purifying foreign substances such as dust from the air introduced into the gas inlet member, and accordingly, the communication hole 366 is blocked to prevent gas from being introduced into the nano bubble generating part 340.

The dispersing member 30 is mounted to the gas inlet 360, and disperses the gas introduced into the gas inlet 360 so that the gas introduced when the gas in the nano bubble generating part 340 is mixed can be mixed with the liquid.

In more detail, the dispersing member 380 is installed in the mounting recess 364a of the gas inlet member 364, and disperses the gas to make the gas fine primarily.

Thereafter, the gas having passed through the dispersing member 380 and having been made fine primarily is introduced into the nano bubble generating part 340 through the communication hole 366. Then, the gas introduced into the nano bubble generating part 340 is made fine secondarily by the liquid flowing along the nano bubble generating part 340 to be mixed with the flowing liquid.

That is, the gas having been made fine primarily and exiting from the communication hole 266 is made fine secondarily as if the gas is divided by the liquid of a relatively high speed flowing through the nano bubble generating part 340 to be mixed with the flowing liquid.

Meanwhile, the dispersing member 380 may be formed of a porous material having a diameter smaller than 1 μm so that the penetrating gas can be made fine.

As described above, as the gas introduced into the nano bubble generating part 340 through the dispersing member 380 can be made fine and be introduced into the nano bubble generating part 340, a generation rate of the nano bubbles can be improved.

Meanwhile, although not illustrated, a nozzle tip (not illustrated) may be mounted to the cleaning liquid ejection hole 224 of the cleaning device 220, and accordingly, the ejected cleaning liquid is dispersed to be discharged from the cleaning device body 220.

As described above, since gas may be introduced into liquid flowing along the nano bubble generating part 340 through the gas inlet 360 due to a pressure difference between the nano bubble generating part 340 and the outside of the nozzle body 320 to generate nano bubbles, the gas can be introduced into the flowing liquid without using a separate unit for mixing bubbles to generate nano bubbles.

That is, gas can be introduced into flowing liquid without using a separate unit, such as a compression pump for compressing gas, for mixing of bubbles to generate nano bubbles.

Further, since the gas can be introduced into the flowing liquid without using a separate unit for mixing bubbles to generate nano bubbles, noise generated by a separate unit for introducing the gas can be reduced, and manufacturing costs can be reduced and the nano bubble generating nozzle can be miniaturized.

In addition, since the gas can be introduced into the flowing liquid without using a separate device, such as a compression pump for compressing the gas, for mixing bubbles, vibrations generated by a separate unit can be reduced, and accordingly, a phenomenon where the generated nano bubbles disappear can be mitigated.

Further, since a distance by which nano bubbles are moved can be reduced by simplifying the structure of the nano bubble generating nozzle, a phenomenon where nano bubbles generated by growth and breaking of nano bubble nuclei in the passage 122 of the nozzle body 120 disappear before a discharging operation can be mitigated.

As the gas introduced into the gas inlet 360 through the dispersing member 380 can be made fine and be introduced into the liquid, a generation rate of the nano bubbles can be improved.

Meanwhile, the cleaning liquid containing nano bubbles can be discharged through the nano bubble generating nozzle 300.

In addition, since a structure of the nano bubble generating nozzle 300 for generating nano nozzles is simple, the cleaning liquid containing nano bubbles can be discharged and the device can be miniaturized at the same time. That is, the oral cleaning device 200 can be miniaturized.

Further, since the cleaning liquid containing nano bubbles can be discharged, an effect by which the liquid containing nano bubbles reaches a target object so that the nano bubbles disappear, that is, the vibration and negative ion effect can be realized.

In addition, as the liquid containing nano bubbles can be discharged, an effect by which the liquid containing nano bubbles reaches a target object, such as teeth or gums, so that the nano bubbles disappear, that is, the vibration and negative ion effect can be realized.

Hereinafter, an operation of the oral cleaning device according to the embodiment of the present invention will be described with reference to the accompanying drawings.

Figure 8:
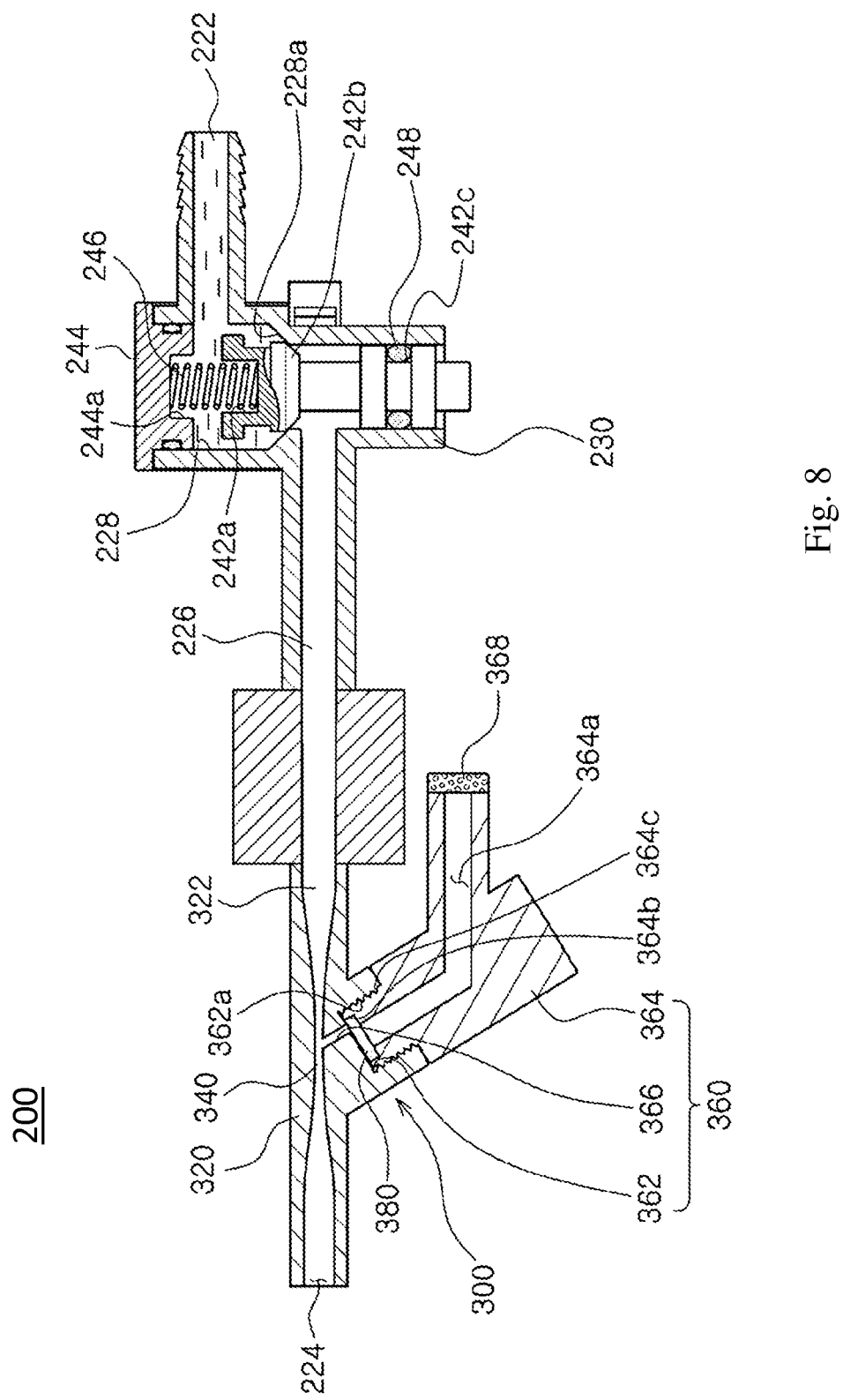
FIGS. 8 and 9 are views illustrating an operation of the oral cleaning device according to the embodiment of the present invention.
Figure 9:
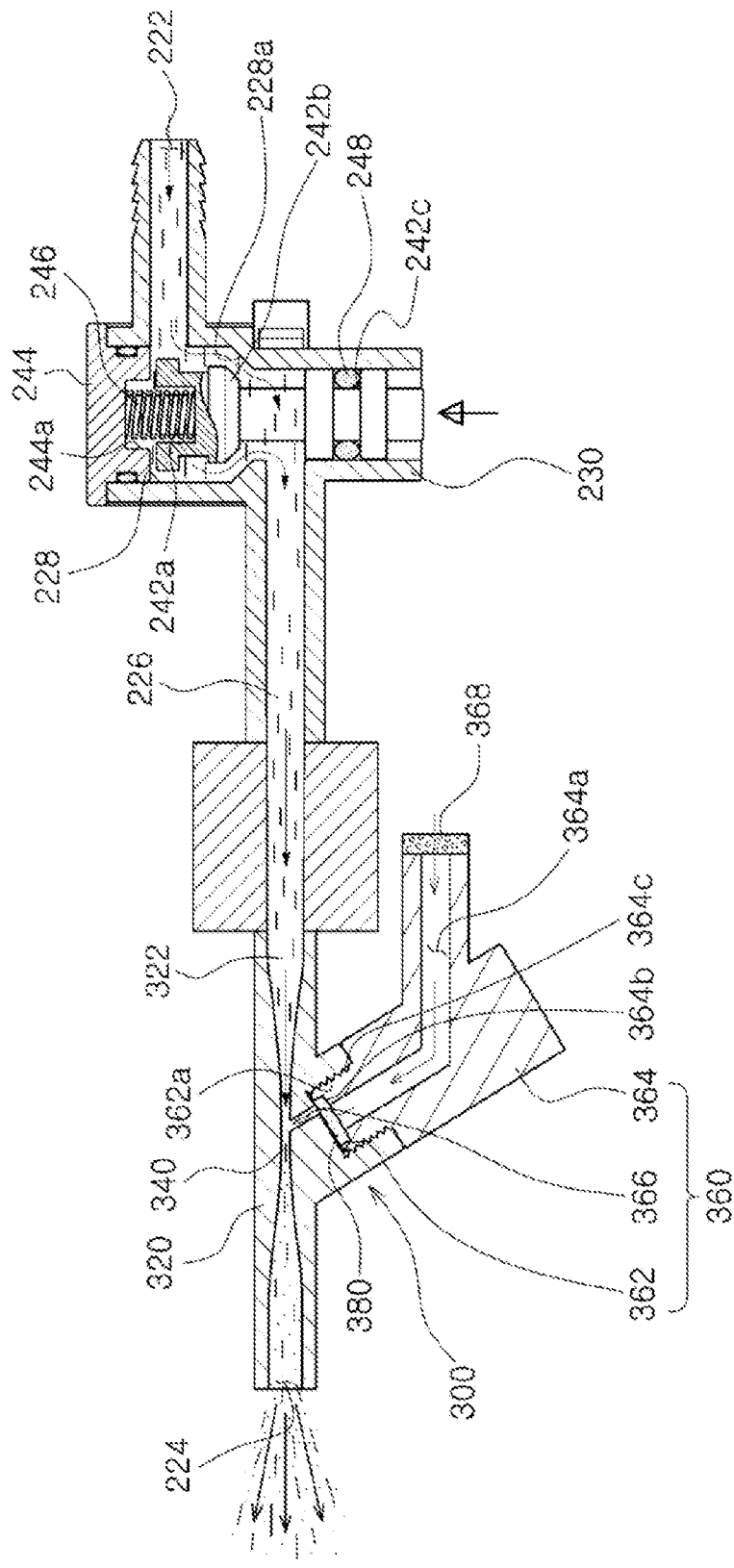

FIGS. 8 and 9 are views illustrating an operation of the oral cleaning device according to the embodiment of the present invention.

That is, FIG. 8 is a view describing a state where cleaning liquid is not introduced into the oral cleaning device according to the embodiment of the present invention, and FIG. 9 is a view describing a state where cleaning liquid is introduced into the oral cleaning device according to the embodiment of the present invention.

First, referring to FIG. 8, when a user does not press the opening/closing member 242, the opening/closing member 242 is disposed at an original position by the resilient member 246. Then, the opening/closing part 242b of the opening/closing member 242 is disposed to contact the inclined surface 228a. Accordingly, the cleaning liquid introduced into the cleaning liquid inlet 222 cannot flow further.

Thereafter, the opening/closing member 242 is pressed by the user as illustrated in FIG. 9, the opening/closing member 242 is moved along the guide part 230 while compressing the resilient member 246, in which case the opening/closing part 242b of the opening/closing member 242 is disposed to be spaced apart from the inclined surface 228a.

Accordingly, the cleaning liquid introduced into the cleaning liquid inlet 222 flows through the mounting part 228 to be introduced into the cleaning liquid passage 226. Thereafter, the cleaning liquid is introduced into the passage 322 of the nozzle body 320 connected to the cleaning liquid passage 226, and then flows along the nano bubble generating part 340.

If the cleaning liquid flows along the nano bubble generating part 340 in this way, an external pressure of the cleaning device body 220 and a pressure in the nano bubble generating part 340 become different, whereby gas is introduced toward the nano bubble generating part 340 a pressure of which is relatively low through the gas inlet 360.

Then, the gas passes through the air filter 368 and is introduced into the gas flow passage 364a of the gas inlet member 364. Accordingly, gas from which foreign substances, such as dust, from the introduced air can be introduced.

Meanwhile, the gas introduced into the gas flow passage 364a passes through the dispersing member 380, and accordingly the gas is made fine primarily.

Thereafter, the gas having passed through the dispersing member 380 flows along the communication hole 366 to be finally introduced into the nano bubble generating part 340. Then, the gas is made fine secondarily as if the gas is divided by the liquid of a relatively high speed.

Consequently, the gas introduced into the nano bubble generating part 340 is changed into nano bubbles and is contained in the cleaning liquid.

Thereafter, the cleaning liquid containing nano bubbles is ejected from the cleaning device body 220 through the cleaning liquid ejection hole 224.

As described above, since the cleaning liquid flowing through the cleaning liquid passage 226 via the nano bubble generating nozzle 300 can contain nano bubbles, the cleaning liquid containing nano bubbles can be discharged.

In addition, the oral cleaning device 200 can be miniaturized by employing a simple structured nano bubble generating nozzle 300.

Further, manufacturing costs of the oral cleaning device 200 can be reduced.

In addition, as the liquid containing nano bubbles can be discharged, an effect by which the liquid containing nano bubbles reaches a target object, such as teeth or gums, so that the nano bubbles disappear, that is, the vibration and negative ion effect can be realized.

What is claimed is:

1. An oral cleaning device comprising:
a cleaning device body including a cleaning liquid inlet through which cleaning liquid is introduced, a cleaning liquid ejection hole from which liquid containing nano bubbles is discharged, and a cleaning liquid passage connecting the cleaning liquid inlet and the cleaning liquid ejection hole;
a nano bubble generating nozzle connected to the cleaning liquid passage such that nano bubbles are contained in the cleaning liquid by introducing gas due to a difference from an external pressure; and
an opening/closing unit mounted to a mounting part provided in the cleaning device body to be connected to the cleaning liquid passage so as to open and close the cleaning liquid passage,
wherein the nano bubble generating nozzle includes:
a nozzle body including a passage passing through an interior thereof to provide a flow path through which liquid flows;
a nano bubble generating part corresponding to a part of the passage, and formed such that a cross-section of the nano bubble generating part becomes smaller and then larger along a flow path of liquid so that the nano bubble generating part has a pressure lower than an external pressure of the nozzle body; and
a gas inlet connected to the nano bubble generating part so that gas is introduced into the nano bubble generating part due to a difference between an external pressure of the nozzle body and a pressure in the nano bubble generating part,
wherein the nano bubble generating nozzle further includes:
a dispersing member mounted to the gas inlet to disperse the gas introduced into the gas inlet so that the gas introduced can be mixed with the liquid,
wherein the gas inlet includes:
an installation recess formed on a side surface of the cleaning device body;
a gas inlet member coupled to the installation recess, and including a gas flow passage integrally formed therein through which gas is introduced, and a mounting recess where the dispersing member is installed; and
a communication hole extending from the installation recess to communicate the nano bubble generating part with the installation recess, and
wherein the opening/closing unit includes:
an opening/closing member slidably coupled to the cleaning device body along a guide part provided in the cleaning device body to open and close the cleaning liquid passage;
a support member fixedly coupled to the cleaning device body to be disposed at an upper portion of the opening/closing member;
a resilient member mounted between the opening/closing member and the support member to provide a resilient force to the opening/closing member; and
a sealing member mounted to a lower end of the opening/closing member to prevent the cleaning liquid from being discharged through the guide part.

2. The oral cleaning device of claim 1, wherein the dispersing member is formed of a porous material having a diameter smaller than 1 μm so that the penetrating gas can be made fine.

3. The oral cleaning device of claim 2, wherein the communication hole is formed such that a cross-section thereof is smaller than or equal to a minimum cross-section of the nano bubble generating part to prevent introduction of the liquid flowing through the nano bubble generating part.

4. The oral cleaning device of claim 2, wherein the gas inlet further includes an air filter installed at an end of the gas flow passage to purify introduced air.

5. The oral cleaning device of claim 1, wherein a ratio of a diameter of a portion of the nano bubble generating part corresponding to a minimum cross-section and a diameter of the passage formed in the nozzle body may be 1:2 to 1:4.

* * * * *